United States Patent
Jenneman et al.

(10) Patent No.: US 10,635,762 B2
(45) Date of Patent: Apr. 28, 2020

(54) RESERVOIR SOURING FORECASTING

(71) Applicant: CONOCOPHILLIPS COMPANY, Houston, TX (US)

(72) Inventors: Gary E. Jenneman, Bartlesville, OK (US); Edward Burger, Dallas, TX (US); Babajide Kolade, Chicago, IL (US)

(73) Assignee: ConocoPhillips Company, Houston, TX (US)

( * ) Notice: Subject to any disclaimer, the term of this patent is extended or adjusted under 35 U.S.C. 154(b) by 200 days.

(21) Appl. No.: 15/331,350

(22) Filed: Oct. 21, 2016

(65) Prior Publication Data

US 2017/0116359 A1  Apr. 27, 2017

Related U.S. Application Data

(60) Provisional application No. 62/245,135, filed on Oct. 22, 2015.

(51) Int. Cl.
| | |
|---|---|
| *G06F 17/50* | (2006.01) |
| *E21B 43/20* | (2006.01) |
| *E21B 41/00* | (2006.01) |
| *E21B 47/10* | (2012.01) |
| *G01N 33/24* | (2006.01) |
| *G01V 9/00* | (2006.01) |
| *E21B 43/24* | (2006.01) |
| *E21B 49/00* | (2006.01) |

(52) U.S. Cl.
CPC ...... *G06F 17/5009* (2013.01); *E21B 41/0092* (2013.01); *E21B 43/20* (2013.01); *E21B 43/24* (2013.01); *E21B 47/10* (2013.01); *E21B 47/1015* (2013.01); *E21B 49/008* (2013.01); *G01N 33/241* (2013.01); *G01V 9/007* (2013.01); *G06F 2217/16* (2013.01)

(58) Field of Classification Search
CPC ... G06F 17/50; E21B 47/1015; G01N 33/241; G01N 33/2882; G01V 9/007
USPC ............ 703/2; 166/263, 366, 305.1; 436/56; 435/29
See application file for complete search history.

(56) References Cited

U.S. PATENT DOCUMENTS

| | | | |
|---|---|---|---|
| 8,813,854 B2 * | 8/2014 | Sahni | E21B 43/20 166/263 |
| 2001/0036667 A1 | 11/2001 | Tayebi et al. | |
| 2007/0255500 A1 | 11/2007 | Pita et al. | |
| 2010/0300682 A1 * | 12/2010 | Thakur | E21B 43/00 166/250.01 |

(Continued)

OTHER PUBLICATIONS

Coombe, et al., "Simulation of Bacterial Souring Control in an Albertan Heavy Oil Reservoir," 10th Canadian International Petroleum Conference (the 60th Annual Technical Meeting of the Petroleum Society), Jun. 16-18, in Calgary, Alberta (2009).

(Continued)

*Primary Examiner* — Thai Q Phan
(74) *Attorney, Agent, or Firm* — Boulware & Valoir

(57) ABSTRACT

A method for modeling reservoir souring using object-oriented numerical solutions separate from reservoir topography is described. Specifically, flow physics are separated into one or more objects, along with one or more H$_2$S generation mechanisms, for modeling on time and spatial scales separate from field scale modeling.

33 Claims, 5 Drawing Sheets

(56) References Cited

U.S. PATENT DOCUMENTS

| | | | |
|---|---|---|---|
| 2011/0146993 A1* | 6/2011 | Sahni | E21B 43/16 166/305.1 |
| 2012/0022841 A1 | 1/2012 | Appleyard | |
| 2012/0059640 A1 | 3/2012 | Roy et al. | |
| 2014/0326463 A1* | 11/2014 | Sahni | E21B 43/16 166/366 |
| 2016/0097106 A1* | 4/2016 | Robinson | C23F 11/08 514/44 R |

OTHER PUBLICATIONS

Haghshenas, Mehdi, Modeling and Remediation of Reservoir Souring, Ph.D. Thesis, The University of Texas at Austin (2011).

Lambo, et al. Competitive, microbially mediated reduction of nitrate with sulfide and aromatic oil components in a low-temperature, Western Canadian oil reservoir. Environ. Sci. Technol. 42: 88941-8946 (2008).

Burger, et al., Forecasting the effect of produced water reinjection on reservoir souring in the Ekofisk field, Corrosion 2006, National Association of Corrosion Engineers' 61st Annual Conference and Exhibition, Mar. 12-16, San Diego, CA, NACE 06661 (2006).

Burger, et al., A mechanistic model to evaluate reservoir souring in the Ekofisk field, SPE International Symposium on Oilfield Chemistry, Houston, TX, Feb. 2-4, SPE 93297 (2005).

Burger & Jenneman, Forecasting the effects of reservoir souring from waterflooding a formation containing siderite, SPE International Symposium on Oilfield Chemistry, The Woodlands, TX, Apr. 20-22, SPE 121432 (2009).

Zuluaga, et al. Technical Evaluations to Support the Decision to Reinject Produced Water, SPE Annual Technical Conference and Exhibition, Florence, Italy, Sep. 20-22, SPE 132346 (2010).

Burger, et al., On the partitioning of hydrogen sulfide in oilfield systems, SPE International Symposium on Oilfield Chemistry, The Woodlands, TX, Apr. 8-10, SPE 164067 (2013).

Burger, et al., "The impact of dissolved organic carbon type on the extent of reservoir souring.", SPE International Symposium on Oilfield Chemistry, The Woodlands, TX, Apr. 8-10, SPE 164068 (2013).

International Search Report and Written Opinion issued in connection with corresponding PCT Application No. PCT/US2016/058226 dated Jan. 19, 2016.

* cited by examiner

RESERVOIR SOURING FORECASTING

PRIOR RELATED APPLICATIONS

This application is a non-provisional application which claims benefit under 35 USC § 119(e) to U.S. Provisional Application Ser. No. 62/245,135 filed Oct. 22, 2015, entitled "RESERVOIR SOURING FORECASTING," which is incorporated herein in its entirety.

STATEMENT REGARDING FEDERALLY SPONSORED RESEARCH

Not applicable.

FIELD OF THE DISCLOSURE

The disclosure relates to reservoir modeling techniques, particularly to a system and method for predicting dihydrogen sulfide ($H_2S$) levels.

BACKGROUND OF THE DISCLOSURE

Numerical simulation is widely used in industrial fields as a method of simulating a physical system by using a computer. In most cases, there is desire to model the transport processes occurring in the physical system. What is being transported is typically mass, energy, momentum, or some combination thereof. By using numerical simulation, it is possible to model and observe a physical phenomenon and to determine design parameters, without actual laboratory experiments and field tests.

Reservoir simulation or modeling is of great interest because it infers the behavior of a real hydrocarbon-bearing reservoir from the performance of a model of that reservoir. The typical objective of reservoir simulation is to understand the complex chemical, physical, and fluid flow processes occurring in the reservoir sufficiently well to predict future behavior of the reservoir to maximize hydrocarbon recovery.

Reservoir simulation often refers to the hydrodynamics of flow within a reservoir, but in a larger sense reservoir simulation can also refer to the total hydrocarbon system, which can include not only the reservoir, but also injection wells, production wells, surface flowlines, associated aquifers, and surface processing facilities.

Reservoir simulation calculations in such hydrocarbon systems are based on fluid flow through the entire hydrocarbon system being simulated. These calculations are performed with varying degrees of rigor, depending on the requirements of the particular simulation study and the capabilities of the simulation software being used.

One area of keen interest is $H_2S$ generation and transportation in a reservoir. $H_2S$ is an undesirable component that is produced along with oil, water, and gas from hydrocarbon reservoirs. Crude oil is considered "sour" when a high amount of sulfur impurities in both the hydrocarbon and reservoir.

The levels of produced $H_2S$ are affected by hydrocarbon composition and connate water chemistry of the reservoir, thermal processes related the depositional environment, biological reactions of sulfate reducing bacteria, natural scavenging reactions such as reactions between $H_2S$ and siderite (a $FeCO_3$ mineral), and effects of field production methods, such as water injection. As reservoirs age and water injection is implemented for pressure maintenance, there is an inherent risk of the reservoir souring, mainly as a result of the downhole activity of sulfate-reducing bacteria ("SRB") that metabolize the organic compounds in the reservoir and transfer electrons to sulfur, instead of oxygen (See FIG. 1).

Reservoir souring is very detrimental because $H_2S$ is a highly toxic and flammable gas. The lethal concentration is 800 ppm for 50% of humans exposed for 5 minutes, poisoning several different systems in the body. It forms a complex bond with iron in the mitochondrial cytochrome enzymes, thus preventing cellular respiration. Therefore, reservoir souring raises major safety concerns in field operations.

Corrosion is another detrimental effect of hydrogen sulfide. In the presence of moisture, $H_2S$ can act as a catalyst in the absorption of atomic hydrogen in steel, promoting sulfide stress cracking ("SSC") in high strength steels, thus necessitating the deployment of chemical scavengers or corrosion inhibitors to protect the production facilities. Installation of chemical sweetening systems to meet export or refinery specifications is another complexity (and expense) caused by reservoir souring.

Hence, reservoir souring is both dangerous and can greatly increase the operational costs of oil production, especially when it is unpredicted in the field development plan. In addition, contamination of the produced hydrocarbons with $H_2S$ contamination reduces the sale value of products. Thus, robust predictions of concentrations and volumes of $H_2S$ that will be produced over the life of the field is important for new field development facilities basis of design, design of wells and material selections, asset and operating integrity assurance, HSE, export gas specification, and overall asset management.

Reservoir model for forecasting $H_2S$ production during the life of a field has been developed, for example, SourSimRL, which has been used in several studies to enable metallurgical selection and cost-effective mitigation strategies to be considered. This model is based on inputted information relating to reservoir's nutrients, and composition of injection and formation water. It is possible to simulate corrective action processes like biocide and nitrate injection. However, this model is somewhat simplistic. Further, SourSim was developed by Oilplus for a consortium of oil companies and the proprietary property is not available for update or refinement.

SPE-164068, for another example, describes a reservoir souring model used to help explain the lack of nitrate treatment effectiveness at controlling reservoir souring and $H_2S$ production from a moderately hot oilfield. The model was modified to include the direct metabolism of sulfate-reducing and nitrate-reducing bacteria by stoichiometric reactions between dissolved organic carbons ("DOC"), sulfate and nitrate. The availability of both volatile fatty acids and benzene, toluene, ethylbenzene, and xylene ("BTEX") components as the DOC source within the reservoir was provided by partitioning these components from residual oil within the waterflood regions of the reservoir. Results indicated that the water-soluble volatile fatty acids ("VFAs") would be consumed rapidly in the near-injector region by both SRB and nitrate reducing bacteria ("NRB"), with the $H_2S$-biogeneration front moving into the reservoir where sulfate and DOC are able to mix and react. Oil-soluble BTEX components, however, continually partition from the oil into the water phase, even near the injector, allowing SRB activity to proceed throughout the waterflooded regions of the reservoir.

The historical trend of the calculated sour water concentration ("SWC") is an indicator of the DOC source, with continually increasing field-wide SWC representing a strong likelihood of BTEX involvement in SRB activity. While a seemingly insignificant contribution of BTEX might not make a measurable difference in $H_2S$ production during the initial stages of a souring field's operation, significantly elevated future $H_2S$ production can result, even with nitrate treatments. Routinely analyzing produced water samples for all DOC components from the start of waterflood is important in identifying the DOC source for microbial activity.

Note, however, that this model didn't account for nitrite inhibition of SRB.

To fully understand and be able to predict reservoir souring accurately, it is important that further progress is made in obtaining relevant data on plausible microbiological and chemical routes and the rate and extent of contributing reactions. It is equally important to account for the relative solubility/partitioning data of $H_2S$ between oil/water, water/biofilm, water/gas phases in the reservoir and in process equipment.

The basis of the available models depend on a number of factors, the most important of which is the rate at which water moves through the reservoir. Other uncertainties include the degree of scavenging by reservoir rock (particularly iron minerals such as siderite), watercut, the type of water used (seawater versus produced water re-injection ("PWRI") or waste-water injection (WWI)), producing gas oil ratio ("GOR") and nutrient supply.

Most $H_2S$ models use 'generic' nutrient types to represent the various nutrients due to natural variation and uncertainties:

SRBs+[C,N,P nutrients]+Sulphate ions→Sulphide→$H_2S$

Generally, the more nutrients and sulphate ions present in injected water, the greater the amount of $H_2S$ generated by SRBs. As formation and injection waters can contain volatile fatty acids (VFAs), ammonium ions, amine and phosphorus compounds (e.g. production chemicals), together with substances such as natural surfactants from produced hydrocarbons, produced water can be much richer in nutrients than injected seawater. This means that the souring potential associated with produced water re-injection (PWRI) can be much higher than for seawater injection (by up to a factor of 2-3).

As $H_2S$ moves through the reservoir, it can interact with the mineralogy, particularly the iron minerals. Sulphide ions react with iron ions dissolving from iron minerals to form iron sulphide solids. This type of reaction causes natural scavenging of $H_2S$ generated by SRB:

Sulphide ions+Iron ions→Iron Sulphide precipitates

The amount of $H_2S$ produced by a well going sour is related to the amount of water produced multiplied by a sour water concentration (usually expressed as ppm w/w). Most of the $H_2S$ is transported through the reservoir in injected water. This sour water concentration can be converted into a calculated gas phase $H_2S$ concentration by partitioning the $H_2S$ between the gas, oil and water at surface (or a maximum value can be obtained by assuming all of this $H_2S$ flashes into the gas phase):

Sour Water Concentration=Mass of $H_2S$ Produced/Mass of Water Produced

In most cases, it is impossible to quantify the effect of the uncertainties on the overall $H_2S$ profiles due to the number of factors involved. Some of these factors are listed below:

Reservoir Heterogeneity and Breakthrough Times: The presence of high permeability streaks or fractures may increase the rate of souring by channeling water through a limited volume of rock to the producers.

Interactions with and Distribution of Mineralogy: The variability of iron mineral distribution and its interaction with injection water will determine how much natural scavenging actually occurs in practice. Other clays and minerals may also have some impact on local pH conditions and interaction with iron species. It is very difficult to quantify precisely how much scavenging is likely to occur in practice, as it is also influenced by kinetics of the dissolution/precipitation/ion exchange reactions taking place.

Surface Partitioning: The influence of kinetics, fluid composition, temperature and pressure on $H_2S$ partitioning between gas, oil, water and biofilm are not very well known. Estimates from thermodynamic calculations and field experience elsewhere tend to suggest the range of values used in the summary tables will apply in practice. Sensitivity to the actual value of the partition coefficients may be up to a factor of 3 in terms of gas phase $H_2S$ concentrations.

Effect of Reservoir Temperature: The reservoir temperature may create a smaller region around the injection wells in which the SRB can survive, although most $H_2S$ generation is thought to occur close to the injection wellbore. The actual temperature of the injection water may have an impact on the rate of conversion of sulphate to sulphide. The variety of bacterial populations (mesophiles, thermophiles, hyperthermophiles, SRBs, NRBs, etc.) means that some species may survive even at very high temperatures, but growth rates may vary and this can influence model accuracy.

Nutrient Input: The precise concentration of nutrients being injected into the reservoir and their effects on population growth of SRB (and other bacteria) are difficult to assess. Much of the modeling has been derived from history-matching of field situations based on known or estimated information from the field or laboratory.

Future Reservoir Management: Any differences in production/injection rates could have an impact on the overall $H_2S$ profile (up or down). For example, prolonged production at higher watercuts than those assumed in the profiles could increase $H_2S$ concentrations. Water shut-off could immediately reduce $H_2S$ concentrations in a well by over 50% by reducing the partitioning effect at lower watercut and by shutting off sour water. Delay in water breakthrough times by reducing rates or increasing injector-producer distances could also be potential souring mitigation techniques.

There remain many challenges with developing robust models for predicting the souring of a reservoir. $H_2S$ concentrations and volumes predictions are complicated by the differing time and spatial scales of the processes that contribute to its production. For example, scavenging reactions are mainly affected by the pore scale, biological processes at the core scale, but the water injection scheme is determined on the field scale, and thermal processes are affected at the reservoir scale. Also the contributing mechanisms have varying degrees of sensitivities to the different physics, such as fluid dynamics, biochemistry, thermodynamics, and heat transfer. This leads to a competition between accurate and reliable prediction of $H_2S$ levels, efficient computation for a long forecast horizon, and ease-of-use and adaptability of a prediction tool for different field development configurations. These factors are hard to incorporate into a prediction model.

Accordingly, it would be advantageous to provide a means for modeling and predicting H$_2$S concentrations and volumes on a multiscale level to account for the different mechanisms affecting H$_2$S generation and transportation. Ideally, this method will take into account the topology of the reservoir, the chemistry and physics involved with H$_2$S generation, and the various H$_2$S generation mechanisms. Ideally, effects of the H$_2$S concentration on e.g. process equipment should also be included to fully understand the economical outlook for a particular model. Thus, there exists a need in the art for more inclusive models that facilitate more accurate prediction of reservoir souring so that the appropriate preventative and protective measures can be in place.

SUMMARY OF THE DISCLOSURE

Our approach to reservoir souring studies is unique in that it combines the scientific knowledge to understand the causes and extent of souring with the engineering knowledge required to address the consequences of souring.

H$_2$S is often produced following the injection of water into a petroleum bearing formation. Knowing (a priori) the H$_2$S mass and gas concentrations that will be produced over the life of the field is important information needed to select and design materials for wells and facilities; plan for safety barriers that may be required; and plan for preventative and mitigative technologies that may be necessary to operate the field economically and safely.

However, our model can also be history matched and recalibrated over the life of the field to ensure that former predictions and forecasts are accurate. This information is useful during operation of the field to determine how well mitigation efforts are working; evaluate alternative mitigation options; determine if alternative materials will be needed; evaluate the impact of new fields and developments in the area; and estimate the amount of H$_2$S scavenger that will be needed to stay within defined H$_2$S limits.

Potentially novel features of the invention include biogeneration of H$_2$S based on indigenous dissolved organic carbon which is used to determine the amount of biogenerated H$_2$S; partitioning of H$_2$S between oil/water/gas used to determine the amount of H$_2$S present in various phases throughout modeling (used for material balancing purposes); adsorption of H$_2$S to siderite (siderite is a sink for H$_2$S in reservoir and accounts for H$_2$S that will not be produced); partitioning of dissolved organic carbon between oil and water which determines the concentration of these nutrients available to the bacteria in the reservoir; and effect of temperature on biogeneration of H$_2$S (temperature will affect the rate and extent of H$_2$S biogeneration in the reservoir). The model uses all these features to predict the final concentration/mass of H$_2$S that is produced at a 3 phase separator or other surface facility where H$_2$S is measured.

The methods disclosed herein pertain to a numerical technique for reservoir souring forecasting. In particular, a multi-scale, object-oriented numerical modeling technique capable of resolving fine scale physics, while preserving computational efficiency of larger scaled physics is described. This will allow for the modeling of and prediction of H$_2$S generation and transport concurrent with oil field development and production schemes. Additionally, the object-oriented design will facilitate easy modifications of the schemes without unduly adding to simulation time.

The present applicant has a computer modeling program, COPRISM, described in SPE121432, SPE93297, and NACE 06661, each of which is incorporated by reference for all purposes. COPRISM is a modeling system that predicts the final concentration/mass of H$_2$S using the biogeneration of H$_2$S based on indigenous dissolved organic carbon, partitioning of H$_2$S between oil/water/gas, adsorption of H$_2$S to siderite, partitioning of dissolved organic carbon between oil and water, and the effects of temperature. Algorithms for seawater injections, freshwater injections or mixes of both are used in the modeling program wherein the algorithms are calibrated using historical match data. However, this modeling program assumes that all microbial H$_2$S activities occur in fractures and not on the pore level. Further, the model does not account for each mechanism's sensitivity to the different physics as play, i.e. fluid dynamics, biochemistry, thermodynamics, heat transfer, or the different time scales to which the mechanism occur.

The present method expands upon the abilities of COPRISM by accounting for pore level activity. The technique described herein leads to a fit-for-purpose software design for research scientists and engineers and facility engineers to forecast reservoir souring, forecast topside H$_2$S production rate, design souring mitigation strategies, select well metallurgy, and aid in export gas/fuel gas specifications.

As noted above, robust predictions of concentrations and volumes of H$_2$S that are produced over the lifetime of a well are important for new field development facilities. However, this prediction is complicated by the fact that H$_2$S is generated at different times over the production lifetime and affects the reservoir on different spatial scales (pore v. core v. field scale) and the equipment on different temporal scales.

The currently disclosed modeling technique separates flow physics from network topology of the reservoir and encapsulates the flow physics in reusable objects. This allows the model to calculation H$_2$S generated by multiple mechanism at differ time periods or different spatial levels separately for a given field development configuration. This will allow for prediction of when and how much H$_2$S will be generated and allow for planning of such.

The flow physics of interest include flow network parameters such as location, connectivity, size and boundary conditions, as well as fluid dynamics, thermodynamics, chemical reactions, and heat transfers. H$_2$S generation mechanisms such as biological reactions of sulfate reducing bacteria (SRB), natural scavenging reactions, thermal reactions, interaction between H$_2$S and hydrocarbons, reactions between H$_2$S and water injection, and/or a combination thereof can also be encapsulated by an object.

The main idea behind this modeling technique is to encapsulate the rigorous model physics in objects that may be configured for different field development strategies, and additionally allow resolution of the different physics on different time scales. This is especially important for H$_2$S predictions because of the need to consider different mechanisms that have different temporal and spatial scales than the large scaled physics of the reservoir.

The objects created in the modeling technique can address material streams, boundary conditions (BC), i.e. flow BC and temperature/pressure BC, top-side separator, and reservoir elements in one or two dimensions. The objects to be created include, but are not limited to, a Reservoir Element object, Well object, Thermodynamics object, Boundary Condition object, Separator object, Mixer object, Biochemistry object, Chemistry object, and/or a Simulation object. Any combination of these objects can be used in a single model.

The Reservoir Element object is the workhorse of the disclosed technique and would be a hierarchical object that can incorporate features from other objects. This object will enforce mass balance, compute flow rate, heat transfer, reactions within the reservoir thermodynamics, compositions of the different phases, pressures, and saturations as a function of location and time. In some embodiments, the Reservoir Element object may be a transient, one-dimensional, variable flow area, multiphase, compositional reservoir simulator that enforces mass balance, computes thermodynamics, fluid dynamics, chemical kinetics, and heat transfer. In other embodiments, the Reservoir Element object is a two-dimensional.

Core inputs to the Reservoir Element object are initial conditions & composition, geometry, flow area, column, porosity, bulk density, permeability, imbibition and drainage relative permeabilities, skill friction, $S_{ORW}$ capillary pressures, reactive substrates descriptions and/or reaction mechanisms, and heat transfer characteristics (Cp, k) and/or heat transfer model.

The Reservoir Element object can also inherit data and/or features from other objects. For example, it can inherit the data and numerical methods of a Biochemistry object that computes kinetics of biochemical reactions of reactive substances at the pore/core scale.

If the properties of the reservoir are homogenous, only one Reservoir Element object is needed. However, for more complex systems, multiple Reservoir Element objects may be needed to fully describe the system.

The Thermodynamic object would be capable of computing three-phase T-P/H-P flash for an arbitrary large number of components and would account for effects of pH and ionic strength on the partition of $H_2S$ into the different phases.

The Boundary Condition objects would contain state conditions such as temperature and pressure and flow rate (material stream) boundary conditions.

The Well object would set production profiles and bottom-hole conditions; simulation objects would facilitate parametric studies and optimization calculations.

The Mixer object would model the multiple material stream mixes and perform h-P flashes.

The Chemistry object would be capable of performing calculations related to the flow physics or chemical reactions that generate $H_2S$. In some embodiments, this involves time-based chemical kinetics calculations. In others, it involves calculations related to the scavenging reactions.

A Biochemistry object could account for various parameters that can affect the growth rate of SRB bacteria (such as essential elements, toxic elements, salts, pH, $O_2$ content, etc.), potential biocide use, the strains of SRB present, and/or the rate of the biochemical reactions therein.

Simulation objects include simulation directions such as "Adjust"/"Target", calibrate functions.

A sample depiction of an exemplary model is shown in FIG. 2. As a rule of thumb, the model must include at least one Reservoir Element object and one Simulation object.

In FIG. 2, the multiple Reservoir Element objects are used to calculate heating information for water injections (horizontal row) and reservoir pressure information (vertical row) for a given field scheme. Should part of the scheme be changed, i.e. remove a Reservoir element in the injection row, then the object can easily be removed without altering the calculations performed by the other Elements.

The numerical solution of the governing equations of the Reservoir Element and other objects in a given model would employ multi-scale methods and parallel time matching to effectively resolve stiff differential equations that occur in small time and length scales, while resolving other mechanisms at larger time steps. This design preserves accuracy and optimizes computational efficiency even for long (>20 years) forecast windows.

In accordance with the method, a computer-implemented system for modeling a field development scheme including objects that represent the physics and underlying mechanisms of the field being developed is disclosed. A user interface is provided for specifying parameters for each object, and a plurality of formulas prescribe each object's contribution to various aspects of the proposed field scheme, reservoir features, souring mechanisms, and any other feature of the field that needs to be included in the forecast.

The objects can be used with existing simulation programs such as COPRISM or SourSimRL. The objects can be programmed in any language, particularly C++, Java, HTML, VMI, Python, Ruby and integrated into the simulation program.

The particular objects and their underlying calculations, mechanism, and information will depend on the field to be modeled, the expected mechanisms from e.g. saltwater v. fresh water injections, and reservoir composition. Further, the type of forecasting desired will dictate which objects are needed for a given model. When forecasting bio-generated reservoir souring, it is expected that a simple description of the field layout is needed. However, more intensive descriptions may be necessary when modeling forecasts and metallurgical interactions.

To use the techniques herein, an input file will be uploaded onto a computer running a simulator program. The input file will contain run specifications such as the length of the prediction forecast, field configuration, topography of the reservoir of interest, and the like.

For ease of processing, some embodiments of the specification will use simplified compositions for the reservoir wherein wax, asphaltenes or hydrates are not included as not having an impact on $H_2S$ generation.

The programmed object(s) will also be uploaded to the system. This is a collection of information that describes each object needed in the particular simulations. The element identification and flow network description (i.e. what is on the left and right of each element) will then be added to the simulator. From there, user preferences such as plotting and reporting specifications will be selected. The simulation will then proceed using the uploaded data and objects.

In some embodiments, the computer will employ parallel computation using multicore processors. In others, multiple computers may be connected to handle the simulation. The numerical solution may also employ parallel computation on graphical processing units (GPUs) whose plentiful cores provide cheap scalability for the design.

The results are a multi-scale forecast of reservoir performance and can include reservoir souring forecasting that can be viewed on different time scales over the entire production timeline. The forecast can be broken down into $H_2S$ generation by individual mechanism, including microbial and injection related activity. Additionally, depending on the initial input, predictions regarding $H_2S$ generation on equipment (i.e. metallurgical interactions) and asset use can also be obtained.

In one embodiment, the modeling is performed using COPRISM. COPRISM uses a history matching process to adjust values for the parameters in these calculations such that the computed $H_2S$ production (rate and concentration) is comparable to the measured production. By using COPRISM, the constants in the calculations used within the objects can be calibrated and adjusted for a better prediction. COPRISM will be used in combination with the object-oriented GUTS-API software.

This summary is provided to introduce a selection of concepts that are further described below in the detailed description. This summary is not intended to identify key or essential features of the claimed subject matter, nor is it intended to be used as an aid in limiting the scope of the claimed subject matter.

As used herein, "object" means a block of code having all the properties including shape, behavior, equations, relations, performance data, and transport requirements, along with embedded links to relevant code requirements and test results, for a given aspect of the modeled scenario.

As used herein, "hydrocarbon field" refers to an area having subsurface hydrocarbon zones.

As used herein, "field development configuration" refers to development plans that comprise all activities and processes required to develop a field and attempts to provide the best technical solution for field optimization. Modifications are made to the configuration until a final development plan with the optimal solutions are created. Features included therein include well number, depth, orientation, temperature, pressure, flow, and the like.

As used herein, "field layout" refers to the schematic of hydrocarbon recovery equipment in a field of interest. Exemplary equipment include injectors, producers, and separators.

As used herein, "nodes" refers to intersections of one or more grid cells.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention.

The following abbreviations are used herein:

| ABBREVIATION | TERM |
| --- | --- |
| BC | Boundary conditions |
| BTEX | benzene, toluene, ethylbenzene, and xylenes |
| COPRISM | ConocoPhillips Reservoir Souring Model |
| Cp | Heat capacity |
| DOC | Dissolved organic carbons |
| GOR | Gas Oil ratio |
| GUTS | Grand Unified Thermodynamic Simulator |
| GUTS API | GUTS Application Program Interface |
| hNRB | heterotrophic NRB |
| K | Thermal conductivity |
| NRB | nitrate reducing bacteria |
| PWRI | Produced water re-injection |
| SO-NRB | sulfide oxidizing, nitrate reducing bacteria |
| Sorw | Residual oil saturation to waterflood |
| SRB | sulfate-reducing bacteria |
| VFA | VOLATILE FATTY ACIDS |
| WOR | Water oil ratio |
| HSE | Health, Safety, Environment |
| SSC | sulfide stress cracking |
| SWC | Sour water concentration |
| WWI | Waste-water injection |

DESCRIPTION OF EMBODIMENTS OF THE DISCLOSURE

Figure 1A:
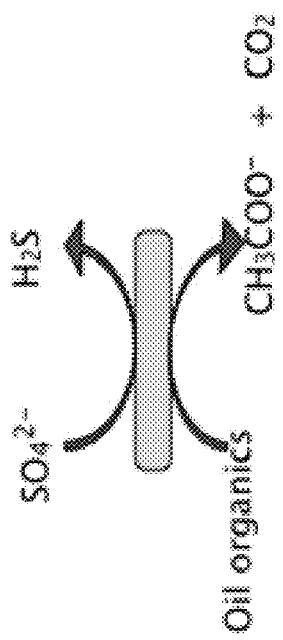
FIG. 1A Sulfate reduction to $H_2S$ by the SRB.
Figure 1B:
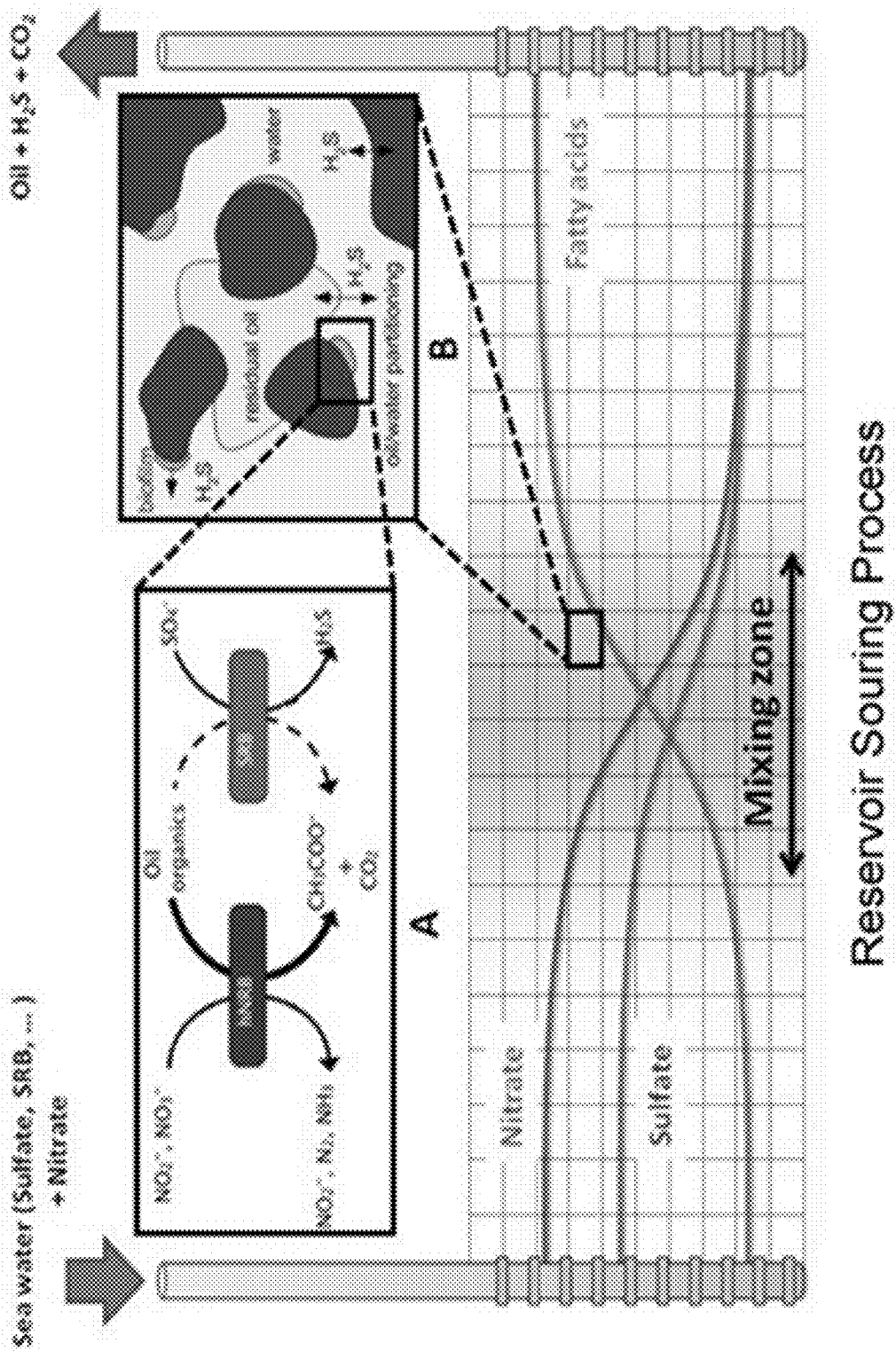
FIG. 1B. Reservoir souring by SRB.
Figure 2:
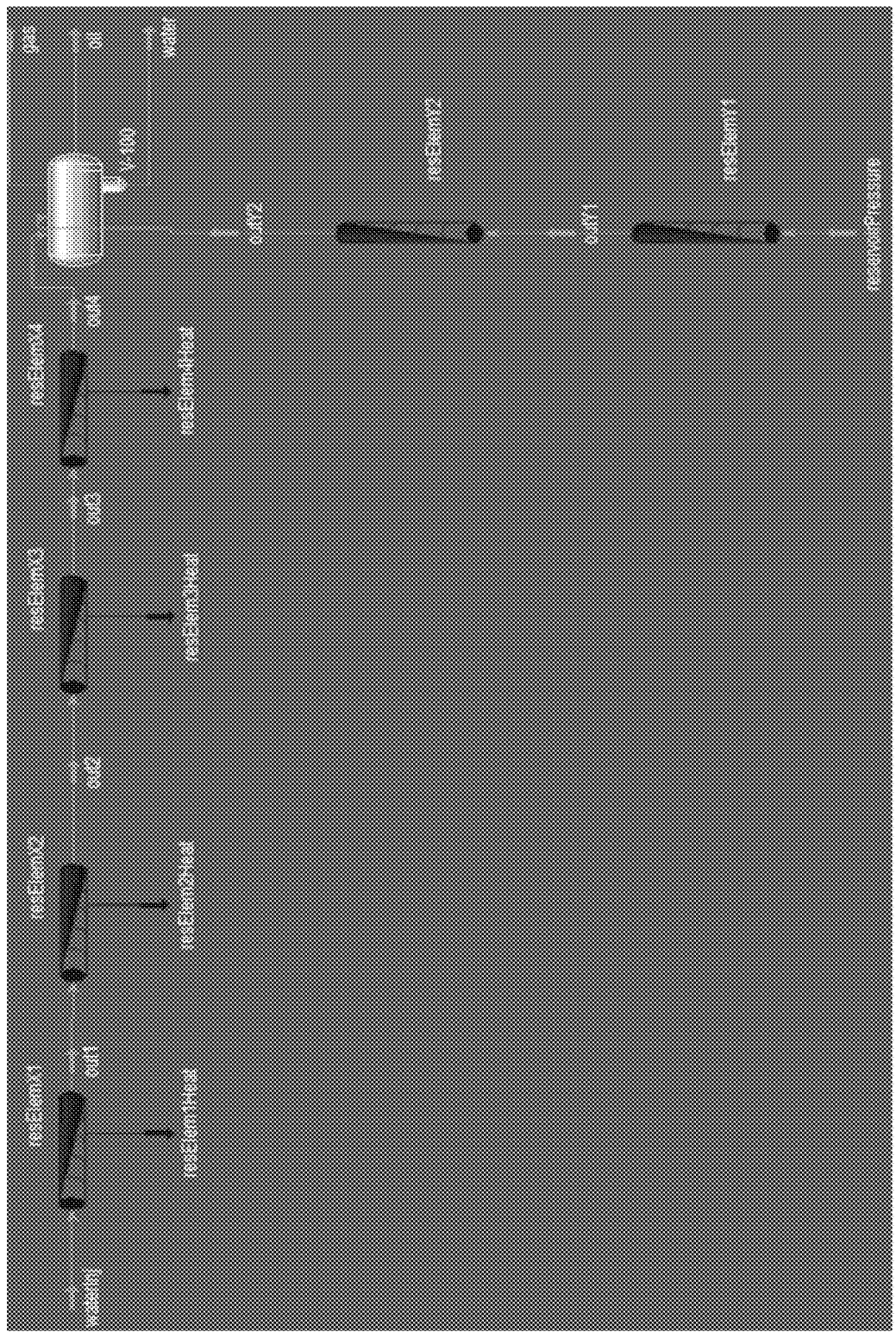
FIG. 2. Depiction of object orientated model according to one embodiment.

The disclosure provides a novel approach to reservoir souring forecasting using an object-oriented model. This type of model allows the user to run calculations and detailed forecasting analysis for different mechanism having differing temporal and spatial scales while preserving the model's larger scale physics and field development configuration.

The prediction and forecasting of $H_2S$ concentrations provided by the currently described systems will improve project cost, operability, safety, and commercial issues.

The present methods includes any of the following embodiments in any combination(s) of one or more thereof:

In one embodiment, a simulation of a hydrocarbon field development is provided where a computer having one or more parallel graphics processing unit (GPU); process historical data for a hydrocarbon field; by inputting, into said GPU, the network topography, field layout, fluid description, and reservoir characteristics of one or more field configurations to create a field model; utilizing object-oriented software, on said GPU, for dividing the flow physics and H2S generation mechanisms of one or more fluids for said one or more field configurations into a plurality of individual basic elements of appropriate units for individual calculation so that the behavior of each individual basic element can be analyzed separately, wherein at least one of said basic elements incorporates said historical data; defining one or more time scales and/or one or more spatial levels for simulating one or more individual basic elements; simulating H2S generation and transport and fluid flow for at least one field model and one or more individual basic elements over said time scales and/or spatial level; and, displaying the results of said simulating step.

In another embodiment, souring is modeled within a reservoir on a computer having at least one parallel graphics processing unit (GPU), by dividing a reservoir topology into a finite number of grid cells that forms a grid of the reservoir; defining interaction regions contained within adjacent grid cells in the grid; inputting, onto said GPU, a description of a field layout for said reservoir topology, and historical data for said reservoir; utilizing object-oriented software, on said GPU, for dividing the flow physics and H2S generation mechanisms for one or more fluids injections for each of said interaction regions into a plurality of individual basic elements of appropriate units for individual calculation so that the behavior of each individual basic element can be analyzed separately; defining one or more time scales and/or one or more spatial scales; performing, using the computer, H2S generation and transport forecast operations for said fluid injection for each interaction region for said time scales and said spatial scales using a plurality of said individual basic elements and said field layout and said historical data; and outputting the model of souring.

In an additional embodiment, reservoir souring for a field development configuration is forecast by providing a computer having at least one parallel graphics processing unit (GPU) and a graphical user interface (GUI) display; inputting, on said GPU, the network topography, field layout, historical reservoir data and the fluid flow physics of a reservoir field configuration, wherein said fluid is freshwater, seawater and/or a combination thereof; modeling said flow physics to form at least one flow physics model, wherein at least one model incorporates said historical reservoir data; encapsulating said at least one flow physics model as a first object, representing one or more predetermined souring mechanisms as an second object; displaying said network topography, field layout and said objects on said GUI display; applying at least one first object and at least one second object to said network topography; and, calculating the reservoir souring for said reservoir field configuration.

In some embodiments, simulation results for one or more field configurations are compared; the configuration with the lowest $H_2S$ generation is selected; and field development plan can be developed. Individual basic elements may contain network parameters such as location, connectivity, size, boundary conditions, fluid dynamics, thermodynamics, chemical reactions, heat transfer rates, or combinations thereof. $H_2S$ generation mechanisms include biological reactions of sulfate reducing bacteria (SRB), natural scavenging reactions, thermal reactions, interaction between $H_2S$ and hydrocarbons, reactions between $H_2S$ and water injection, reactions between $H_2S$ and production equipment, and combinations. Reservoir characterization data may includes initial conditions & composition, geometry, flow area, column, porosity, bulk density, permeability, imbibition and drainage relative permeabilities, skill friction, Sorw, capillary pressures, reactive substrates descriptions or a combination thereof. Hierarchical objects may be incorporated as basic elements from other individual basic element, including a Reservoir Element. Spatial levels may be pore, core and field levels.

Fluid injections may include seawater injections, freshwater injections, waste water injections, produced water re-injection, brine water injection, and mixtures thereof.

A second network topography and a second field layout for a second reservoir field configuration may be incorporated.

A non-transitory machine-readable storage medium, which when executed by at least one processor of a computer, may performs one or more steps of the methods described herein.

Simulation of reservoir models requires solution of equations that govern conservation of mass and energy over time. The process of simulation involves solving the equations over discrete time intervals to monitor changes in reservoir properties. The equations incorporate transport, phase behavior, and reaction relationships from the petrophysical and fluid models. Spatial variations in reservoir properties require the equations to be spatially discretized in a way that corresponds to the grid geometry and topology. Time dependent terms require temporal discretization to monitor the accumulation of mass or energy at grid node locations throughout the reservoir. Spatial discretization methods are selected to ensure accurate representation of grid property heterogeneities.

Previous solutions to modeling $H_2S$ production used ad hoc proprietary models that hardwire the particular reservoir configuration and development pattern of the field into the measurements. This type of technique relies on an operator's expectation on what mechanisms are dominant and then optimizes the model to the identified dominant mechanism. However, such models do not work for alternate field configurations or account for changes in relative important $H_2S$ mechanisms.

Other solutions include piggy-backing a $H_2S$ model on a commercial reservoir simulator, wherein the simulator is designed mainly for detailed flow predictions for short time horizons. Yet others do not even attempt to forecast $H_2S$ and prefer to rely on productions rates, then incorporate mitigation and workovers.

None of these approaches is satisfactory.

An object-oriented approach to forecasting $H_2S$ production is disclosed herein. In object-oriented modeling, blocks of code are assembled like puzzle pieces into larger components. The modeling technique described herein separates flow physics and $H_2S$ generation and transport mechanisms from the reservoir network topology and encapsulates them as reusable objects. This encapsulation programming style allows selective hiding of properties and methods in an object by building an impenetrable wall to protect the code from accidental corruption. Other benefits of encapsulation are a reduction in system complexity, and thus increased robustness, by allowing the developer to limit the interdependencies between software components.

The encapsulated objects are reusable and they can be paired with many different field development configurations. This results in an adaptable prediction tool for the different configurations and for the modeling of many mechanisms over various time scales throughout the production cycle. Thus, the encapsulated models can be extended without compromising the fidelities of previous forecast or solutions.

Each encapsulated object can address one aspect of the system such as chemical mechanisms, biochemical mechanisms, boundary conditions, thermodynamic calculations, production profiles, bottom-hole conditions, optimization calculations and the like. For a given model, only the necessary objects will be used. This allows the same objects to be used over multiple system layouts and to easily be applied to field development configurations as field conditions are modified.

Many features are needed to meet the application areas for forecasting bio-generated reservoir souring. These include a simple description of field layout (injectors, producers, separators); representative time profile of flow rates; time-based flow model, biochemistry mechanism/kinetics; fluid description; rigorous thermodynamics and $H_2S$ partitions; parameter calibration; and flexibility, as well as modular, efficient computation.

The present method is exemplified with respect to the tests below, however, this is exemplary only, and the method can be broadly applied to any reservoir design. The following examples are intended to be illustrative only, and not unduly limit the scope of the appended claims.

Simple Reservoir Model

A model was developed to test the ability to forecast bio-generated souring, $H_2S$ field production rate, souring mitigation, metallurgy selection, export gas/fuel gas specification, and indigenous $H_2S$/thermal generation using a simple reservoir design and the COPRISM software linked with GUTS.

By combining COPRISM with the object oriented method herein, additional information such as forecasting $H_2S$ field production rate, souring mitigation design, metallurgy selection, exportation of gas/fuel gas specifications, and indigenous $H_2S$ and thermal generation forecasting can be obtained.

In this test, a bio-generated reservoir souring forecast model was developed. The model started with a simple description of the field layout and added objects as needed. The field layout for the sample reservoir, shown in FIG. 3, involves only injectors, producers, and separators. The design is flexible enough to meet all of the above application areas for COPRISM and object-oriented modeling. However, this test focuses on the bio-generated reservoir souring forecast.

The flow network of this reservoir was removed from the physics. Thus, changes can be made to the model as needed without hindering the underlying calculations for the $H_2S$ generation.

The objects were created as described above. For the bio-generated reservoir souring forecast, the necessary features include, but are not limited to, a representative time profile of flow rates, a time-based flow model, biochemical mechanism and/or kinetics, fluid descriptions, rigorous thermodynamics/$H_2S$ partition, and parameter calibration. Each of these features are in separate objects to allow for flexible, modular and efficient computation.

Figure 3:
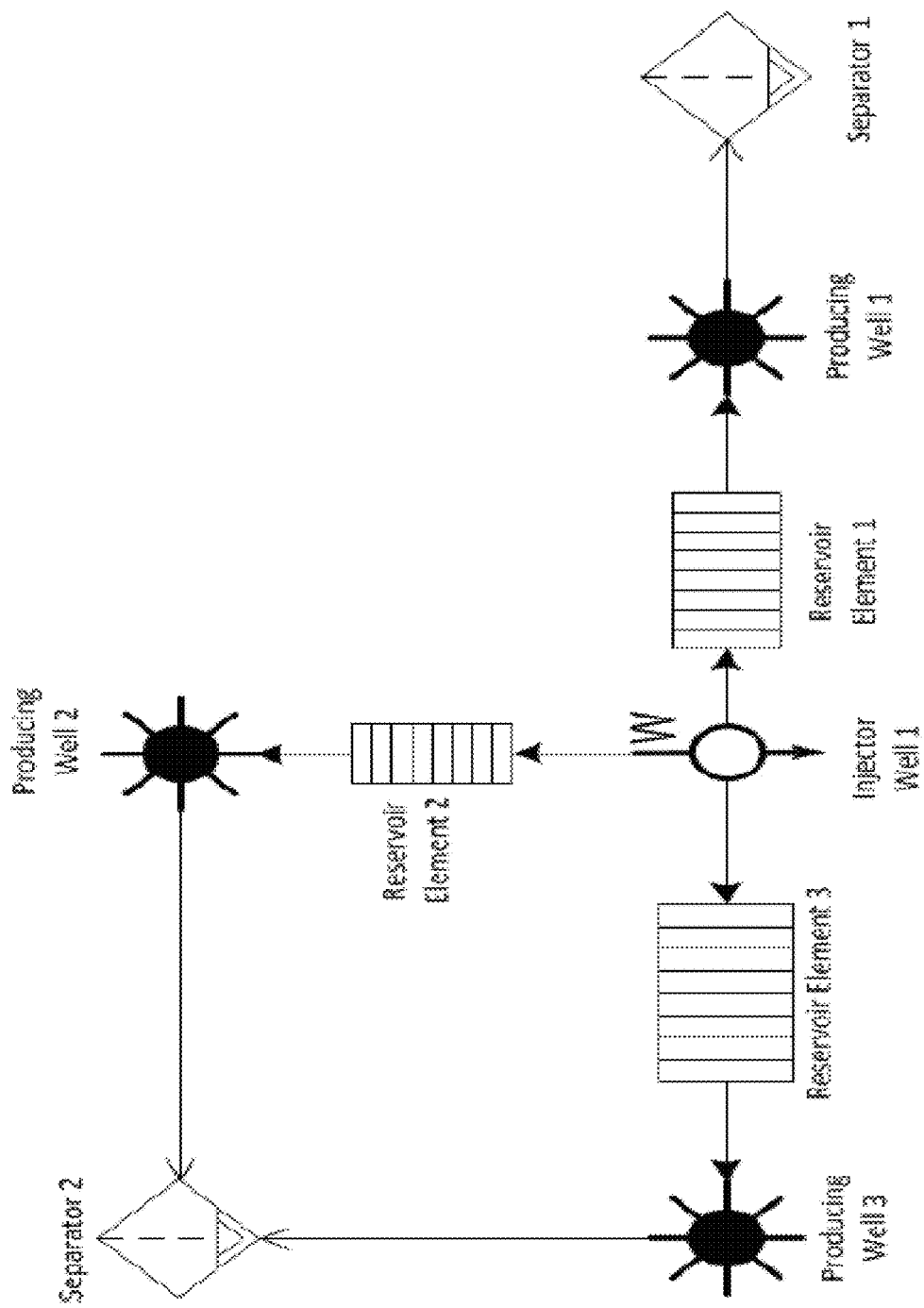
FIG. 3. Simple field layout for forecasting bio-generated souring.
Figure 4:
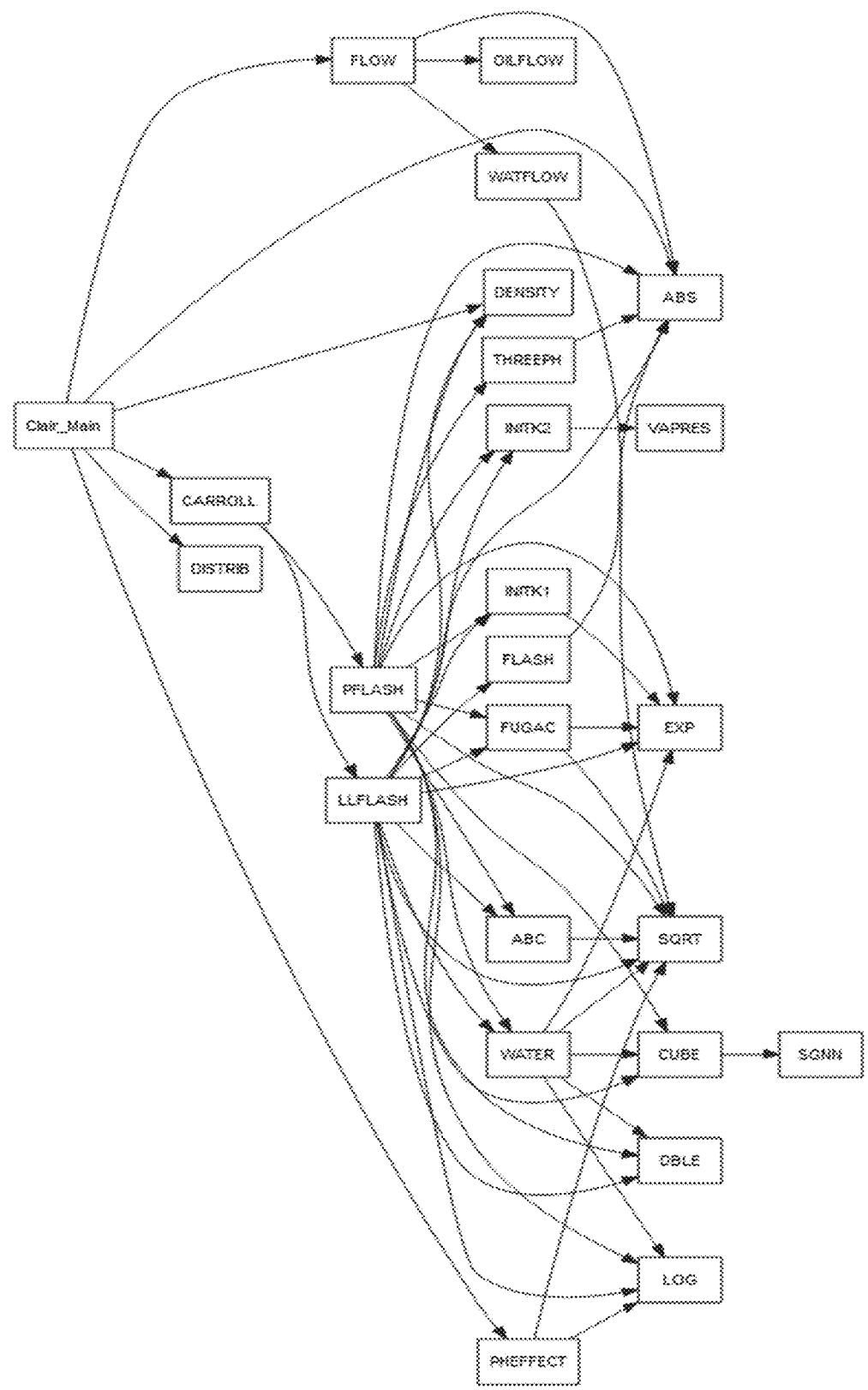
FIG. 4. Model flow.

As seen in FIG. 3, the model also incorporated three reservoir elements.

This field layout was uploaded onto a computer running both COPRISM and GUTS. From there, objects can be added. In this particular test, the model objects test are a Thermodynamics/PVT object, Boundary Condition objects [State (Temp/Pres.) BC, flow rate BC (material stream)], a Reservoir object, a Separator object, a Mixer object, a Chemistry object, and Simulation objects ["Adjust"/"Target", calibrate functions].

The thermodynamics object performed equilibrium calculations using GUTS. This will allow for a simplified reservoir composition to be used when estimating the partitioning of the $H_2S$ between oil, gas, water and/or biofilms. For instance, wax, asphaltenes, and hydrates were not included in the composition input in the present test because they are not expected to affect $H_2S$ partitioning.

The Boundary Condition objects (BC) contain information for the state boundary conditions or the flow rate boundary conditions at one or more nodes. The state BC object sets the pressure, temperature and composition at each node and may be used to model well bottom hole pressure. The flow rate BC object sets the flow rate and composition at each node and may also be used to model the injection well.

The Separator object performs a three-phase T-P flash calculation using GUTS to determine the concentration of $H_2S$ in the live crude, free gas, and water phases in the reservoir.

Hardware may preferably include massively parallel and distributed Linux clusters, which utilize both CPU and GPU architectures. Alternatively, the hardware may use a LINUX OS, XML universal interface run with supercomputing facilities provided by Linux Networx, including the next-generation Clusterworx Advanced cluster management system.

Another system is the Microsoft Windows 7 Enterprise or Ultimate Edition (64-bit, SP1) with Dual quad-core or hex-core processor, 64 GB RAM memory with Fast rotational speed hard disk (10,000-15,000 rpm) or solid state drive (300 GB) with NVIDIA Quadro K5000 graphics card and multiple high resolution monitors, which we normally use with Gedco's Vista™ processing package.

Slower systems could be used but are less preferred since processing and imaging may already be compute intensive.

All of the references cited herein are expressly incorporated by reference. The discussion of any reference is not an admission that it is prior art to the present invention, especially any reference that may have a publication data after the priority date of this application. Incorporated references are listed again here for convenience:

1. Coombe, et al., "Simulation of Bacterial Souring Control in an Albertan Heavy Oil Reservoir," 10th Canadian International Petroleum Conference (the 60th Annual Technical Meeting of the Petroleum Society), June 16-18, in Calgary, Alberta (2009).
2. Farhadinia, "Predictive Modeling of Reservoir Souring," CPGE, University of Texas at Austin, Feb. 2, 2006.
3. Haghshenas, Mehdi, Modeling and Remediation of Reservoir Souring, Ph.D. Thesis, The University of Texas at Austin (2011).
4. Lambo, et al. Competitive, microbially mediated reduction of nitrate with sulfide and aromatic oil components in a low-temperature, Western Canadian oil reservoir." Environ. Sci. Technol. 42: 88941-8946 (2008).
5. NACE 06661: Burger, et al., Forecasting the effect of produced water reinjection on reservoir souring in the Ekofisk field, Corrosion 2006, National Association of Corrosion Engineers' 61st Annual Conference and Exhibition, March 12-16, San Diego, Calif. (2006).
6. SPE 93297: Burger, et al., A mechanistic model to evaluate reservoir souring in the Ekofisk field, SPE International Symposium on Oilfield Chemistry, Houston, Tex., 2-4 Feb. 2005.
7. SPE 121432: Burger & Jenneman, Forecasting the effects of reservoir souring from waterflooding a formation containing siderite, SPE International Symposium on Oilfield Chemistry, The Woodlands, Tex., 20-22 Apr. 2009.
8. SPE 132346: Zuluaga, et al. Technical Evaluations to Support the Decision to Reinject Produced Water, SPE Annual Technical Conference and Exhibition, Florence, Italy, 20-22 Sep. 2010.
9. SPE 164067: Burger, et al., On the partitioning of hydrogen sulfide in oilfield systems, SPE International Symposium on Oilfield Chemistry, The Woodlands, Tex., Apr. 8-10, 2013.
10. SPE 164068: Burger, et al., "The impact of dissolved organic carbon type on the extent of reservoir souring.", SPE International Symposium on Oilfield Chemistry, The Woodlands, Tex., Apr. 8-10, 2013.
11. SPE 173722: Burger, E. D., et al., Injection of Nitrate During PWRI to Reduce $H_2S$ Production in a Bohai Bay Oil Field Offshore China (2015).

The invention claimed is:

1. A simulation method of a hydrocarbon field development configuration, comprising:
   a) providing a computer having one or more parallel graphics processing unit (GPU);
   b) providing historical data for a hydrocarbon field;
   c) inputting, into said GPU, the network topography, field layout, fluid description, and reservoir characteristics of one or more field configurations to create a field model of said hydrocarbon field;

d) utilizing object-oriented software, on said GPU, for dividing fluid flow physics models of a reservior field configuration the flow physics and H$_2$S generation mechanisms of one or more fluids for said one or more field configurations into a plurality of individual basic elements of appropriate units for individual calculation so that the behavior of each individual basic element can be analyzed separately, wherein at least one of said basic elements incorporates said historical data;

e) defining one or more time scales and/or one or more spatial levels for simulating one or more individual basic elements;

f) simulating H$_2$S generation and transport and fluid flow for at least one field model and one or more individual basic elements over said time scales and/or spatial level; and, g) displaying the results of said simulating step.

2. The method of claim 1, further comprising h) comparing simulation results for one or more field configurations; i) selecting the configuration with the lowest H$_2$S generation; and j) creating and implementing a final field development plan to maximize hydrocarbon recovery from said hydrocarbon field.

3. The method of claim 1, where said individual basic elements contain network parameters such as location, connectivity, size, boundary conditions, fluid dynamics, thermodynamics, chemical reactions, heat transfer rates, or combinations thereof.

4. The method of claim 1, where said H$_2$S generation mechanisms are biological reactions of sulfate reducing bacteria (SRB), natural scavenging reactions, thermal reactions, interaction between H$_2$S and hydrocarbons, reactions between H$_2$S and water injection, reactions between H$_2$S and production equipment, and/or a combination thereof.

5. The method of claim 1, wherein said reservoir characterization data includes initial conditions & composition, geometry, flow area, column, porosity, bulk density, permeability, imbibition and drainage relative permeabilities, skill friction, Sorw, capillary pressures, reactive substrates descriptions or a combination thereof.

6. The method of claim 1, wherein at least one individual basic element is a hierarchical object incorporating elements from another individual basic element.

7. The method of claim 1, wherein at least one individual basic element is a hierarchical object incorporating elements from another individual basic element and wherein said hierarchical object is a Reservoir Element.

8. The method of claim 1, wherein said spatial levels are pore, core and field levels.

9. The method of claim 1, wherein said fluid injections comprise seawater injections, freshwater injections, waste water injections, produced water re-injection, brine water injection, and mixtures thereof.

10. The method of claim 1, further comprising inputting a second network topography and a second field layout for a second reservoir field configuration.

11. A non-transitory machine-readable storage medium, which when executed by at least one processor of a computer, perform the method of claim 1.

12. A computer-implemented method of modeling souring within a reservoir, said computer having at least one parallel graphics processing unit (GPU), comprising:

a) dividing a reservoir topology into a finite number of grid cells that forms a grid of the reservoir;

b) defining interaction regions contained within adjacent grid cells in the grid;

c) inputting, onto said GPU, a description of a field layout for said reservoir topology, and historical data for said reservoir;

d) utilizing object-oriented software, on said GPU, for dividing the flow physics and H$_2$S generation mechanisms for one or more fluids injections for each of said interaction regions into a plurality of individual basic elements of appropriate units for individual calculation so that the behavior of each individual basic element can be analyzed separately;

e) defining one or more time scales and/or one or more spatial scales;

f) performing, using the computer, H$_2$S generation and transport forecast operations for said fluid injection for each interaction region for said time scales and said spatial scales using a plurality of said individual basic elements and said field layout and said historical data; and g) outputting the model of souring.

13. The method of claim 12, further comprising h) comparing simulation results for one or more field configurations; i) selecting the configuration with the lowest H$_2$S generation; and j) creating and implementing a final field development plan to maximize hydrocarbon production from said reservoir.

14. The method of claim 12, where said individual basic elements contain network parameters such as location, connectivity, size, boundary conditions, fluid dynamics, thermodynamics, chemical reactions, heat transfer rates, or combinations thereof.

15. The method of claim 12, where said H$_2$S generation mechanisms are biological reactions of sulfate reducing bacteria (SRB), natural scavenging reactions, thermal reactions, interaction between H$_2$S and hydrocarbons, reactions between H$_2$S and water injection, reactions between H$_2$S and production equipment, and/or a combination thereof.

16. The method of claim 12, wherein said reservoir characterization data includes initial conditions & composition, geometry, flow area, column, porosity, bulk density, permeability, imbibition and drainage relative permeabilities, skill friction, Sorw, capillary pressures, reactive substrates descriptions or a combination thereof.

17. The method of claim 12, wherein at least one individual basic element is a hierarchical object incorporating elements from another individual basic element.

18. The method of claim 12, wherein at least one individual basic element is a hierarchical object incorporating elements from another individual basic element and wherein said hierarchical object is a Reservoir Element.

19. The method of claim 12, wherein said spatial levels are pore, core and field levels.

20. The method of claim 12, wherein said fluid injections comprise seawater injections, freshwater injections, waste water injections, produced water re-injection, brine water injection, and mixtures thereof.

21. The method of claim 12, further comprising inputting a second network topography and a second field layout for a second reservoir field configuration.

22. A non-transitory machine-readable storage medium, which when executed by at least one processor of a computer, performs one or more steps of the method of claim 12.

23. A method for forecasting reservoir souring for a field development configuration, comprising:

a) providing a computer having at least one parallel graphics processing unit (GPU) and a graphical user interface (GUI) display;

b) inputting, on said GPU, the network topography, field layout, historical reservoir data and the fluid flow physics of a reservoir field configuration, wherein said fluid is freshwater, seawater and/or a combination thereof;

c) modeling said flow physics to form at least one flow physics model, wherein at least one model incorporates said historical reservoir data;

d) encapsulating said at least one flow physics model as a first object, e) representing one or more predetermined souring mechanisms as a second object;

f) displaying said network topography, field layout and said objects on said GUI display;

g) applying at least one first object and at least one second object to said network topography; and, h) calculating the reservoir souring for said reservoir field configuration.

24. The method of claim 23, further comprising i) comparing simulation results for one or more field configurations; j) selecting the configuration with the lowest $H_2S$ generation; and k) creating and executing a final field development plan to maximize hydrocarbon production.

25. The method of claim 23, where said individual basic elements contain network parameters such as location, connectivity, size, boundary conditions, fluid dynamics, thermodynamics, chemical reactions, heat transfer rates, or combinations thereof.

26. The method of claim 23, where said $H_2S$ generation mechanisms are biological reactions of sulfate reducing bacteria (SRB), natural scavenging reactions, thermal reactions, interaction between $H_2S$ and hydrocarbons, reactions between $H_2S$ and water injection, reactions between $H_2S$ and production equipment, and/or a combination thereof.

27. The method of claim 23, wherein said reservoir characterization data includes initial conditions & composition, geometry, flow area, column, porosity, bulk density, permeability, imbibition and drainage relative permeabilities, skill friction, Sorw, capillary pressures, reactive substrates descriptions or a combination thereof.

28. The method of claim 23, wherein at least one individual basic element is a hierarchical object incorporating elements from another individual basic element.

29. The method of claim 23, wherein at least one individual basic element is a hierarchical object incorporating elements from another individual basic element and wherein said hierarchical object is a Reservoir Element.

30. The method of claim 23, wherein said spatial levels are pore, core and field levels.

31. The method of claim 23, wherein said fluid injections comprise mixtures of seawater injections, freshwater injections, waste water injections, produced water re-injection, and brine water injection.

32. The method of claim 23, further comprising inputting a second network topography and a second field layout for a second reservoir field configuration.

33. A non-transitory machine-readable storage medium, which when executed by at least one processor of a computer, performs one or more steps of the method of claim 23.

* * * * *